United States Patent [19]

Möller et al.

[11] 4,122,280
[45] Oct. 24, 1978

[54] PYRAZOLE DERIVATIVES

[75] Inventors: Eike Möller; Karl Meng, both of Wuppertal; Egbert Wehinger, Neviges; Harald Horstmann, Wuppertal, all of Germany

[73] Assignee: Bayer Aktiengesellschaft, Germany

[21] Appl. No.: 672,302

[22] Filed: Mar. 31, 1976

Related U.S. Application Data

[62] Division of Ser. No. 619,891, Oct. 6, 1975, which is a division of Ser. No. 532,311, Dec. 13, 1974, Pat. No. 4,002,641.

[30] Foreign Application Priority Data

Dec. 20, 1973 [DE] Fed. Rep. of Germany ....... 2363511

[51] Int. Cl.² ............................................. C07D 231/20
[52] U.S. Cl. .................................................. 548/377
[58] Field of Search ..................... 548/377; 260/310 R

[56] References Cited

U.S. PATENT DOCUMENTS

| 2,476,987 | 7/1949 | Martin et al. ................ | 260/310 R |
| 3,819,617 | 6/1974 | Bebenburg et al. ............ | 260/310 R |

FOREIGN PATENT DOCUMENTS 7,023,211  2/1972  France ................................ 260/310 A

OTHER PUBLICATIONS

Chem. Abst., Evans et al., vol. 64, 1966, 9704f.

*Primary Examiner*—Henry R. Jiles
*Assistant Examiner*—Jane T. Fan
*Attorney, Agent, or Firm*—Jacobs & Jacobs

[57] ABSTRACT

Pyrazole derivatives of the formula:

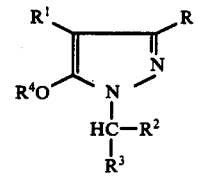

and pharmaceutically acceptable nontoxic salts thereof wherein
  R is hydrogen, trifluoromethyl or alkyl;
  $R^1$ is hydrogen or alkyl;
  $R^2$ is alkyl;
  $R^3$ is a substituted aryl;
  $R^3$ is naphthyl or pyridyl; and
  $R^4$ is $R^5CO$ wherein $R^5$ is alkyl unsubstituted or substituted by 1, 2 or 3 halogen moieties, by alkoxy, or by mono- or dialkylamino; lower alkoxy; dialkylamino; thiophene; phenyl unsubstituted or substituted by 1 or 2 alkyl, trifluoromethyl, alkoxy, nitro or halogen moieties; or a 5- to 7-membered heterocycle unsubstituted or substituted by 1 or 2 halogen, alkyl or nitro moieties; or
  $R^4$ is $Z-SO_2$ wherein Z is alkyl, phenyl or phenyl substituted by 1 or 2 alkyl, halogen, nitro, trifluoromethyl or trifluoromethylsulphonyl moieties; or dichloroquinoxalinyl.

The pyrazole derivatives and their salts are useful as diuretics, saluretics and antihypertensives.

13 Claims, No Drawings

PYRAZOLE DERIVATIVES

CROSS-REFERENCE

This is a division of Ser. No. 619,891 filed Oct. 6, 1975 which is a divisional of Ser. No. 532,311, filed Dec. 13, 1974, now U.S. Pat. No. 4,002,641.

The present invention is concerned with pyrazole derivatives, to a process for their production, to pharmaceutical compositions useful for effecting diuresis, saluresis and treating antihypertension, embodying said compounds as the active ingredient, and to methods of effecting diuresis, saluresis and treating antihypertension which comprises administering said pyrazole derivatives.

It is known in the art that some pyrazole derivatives are antipyretics, analgesics and antiphlogistics (see G. Ehrhard and H. Ruschig, "Arzneimittel" ("Medicaments"), Volume 1, page 148 (1972)).

The use of such compounds as diuretics, saluretics and antihypertensives, however, has not been previously disclosed or suggested.

More particularly, the present invention is concerned with pyrazoles of the formula:

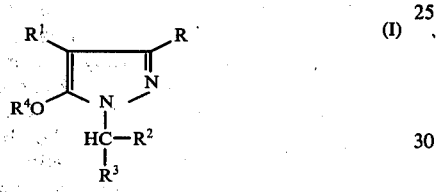

(I)

and pharmaceutically acceptable nontoxic salts thereof wherein

R is hydrogen, trifluoromethyl or alkyl, especially lower alkyl;

$R^1$ is hydrogen or alkyl, especially lower alkyl;

$R^2$ is alkyl, especially lower alkyl;

$R^3$ is aryl, especially phenyl, substituted by:
  (a) one or two of the same or different substituents selected from the group consisting of alkyl especially of 1 to 8 carbon atoms, alkenyl especially of 2 to 8 carbon atoms, alkoxy especially of 1 to 6 carbon atoms, halogen and trifluoromethyl;
  (b) one substituent selected from the group consisting of alkylamino especially of 1 to 4 carbon atoms, dialkylamino especially of 1 to 4 carbon atoms in each alkyl moiety, or said dialkylamino wherein the alkyl moieties are linked to one another and to the nitrogen atom to form a heterocyclic ring, cycloalkyl especially of 5 to 7 carbon atoms, cycloalkenyl especially of 5 to 7 carbon atoms, trifluoromethoxy, nitro, cyano, carbonamido unsubstituted or substituted by 1 or 2 alkyls especially of 1 to 4 carbon atoms, sulphonamido unsubstituted or substituted by 1 or 2 alkyls especially of 1 to 4 carbon atoms, and $SO_n$-alkyl especially of 1 to 4 carbon atoms wherein $n$ is 0, 1 or 2;
  (c) one substituent selected from the group consisting of alkylamino especially of 1 to 4 carbon atoms, dialkylamino especially of 1 to 4 carbon atoms in each alkyl moiety, or said dialkylamino wherein the alkyl moieties are linked to one another and to the nitrogen atom to form a heterocyclic ring, cycloalkyl especially of 5 to 7 carbon atoms, cycloalkenyl especially of 5 to 7 carbon atoms, trifluoromethoxy, nitro, cyano, carbonamido unsubstituted or substituted by 1 or 2 alkyls especially of 1 to 4 carbon atoms, sulphonamido unsubstituted or substituted by 1 or 2 alkyls especially of 1 to 4 carbon atoms, and $SO_n$-alkyl especially of 1 to 4 carbon atoms wherein $n$ is 0, 1 or 2, and by one or two substituents selected from the group consisting of alkyl especially of 1 to 8 carbon atoms, alkenyl especially of 2 to 8 carbon atoms, alkoxy especially of 1 to 6 carbon atoms, halogen and trifluoromethyl; or
  (d) two substituents on the aryl moiety form a branched or unbranched saturated, partially unsaturated or unsaturated 5- to 7-membered isocyclic or heterocyclic ring, which ring can have 1 or 2 oxygen atoms or sulfur atoms; or $SO_n$-alkyl especially alkyl of 1 to 4 carbon atoms wherein $n$ is 0, 1 or 2; or $R^3$ is naphthyl or pyridyl; and $R^4$ is $R^5CO$ wherein $R^5$ is alkyl, especially lower alkyl, unsubstituted or substituted by 1, 2 or 3 halogen moieties especially fluorine or chlorine, by alkoxy especially lower alkoxy, phenoxy or by mono- or dialkylamino especially of 1 to 4 carbon atoms in each alkyl moiety; alkoxy especially lower alkoxy; dialkylamino especially of 1 to 4 carbon atoms in each alkyl moiety; thiophene; phenyl unsubstituted or substituted by 1 or 2 substituents selected from the group consisting of alkyl especially of 1 to 4 carbon atoms, alkoxy especially of 1 to 4 carbon atoms, trifluoromethyl, nitro or halogen; or a 5- to 7- membered heterocycle unsubstituted or substituted by 1 or 2 alkyl moieties especially of 1 to 4 carbon atoms, halogen moieties or nitro moieties; or $R^4$ is $Z-SO_2$ wherein Z is alkyl especially lower alkyl, phenyl or phenyl substituted by 1 or 2 substituents selected from the group consisting of alkyl of 1 to 4 carbon atoms, halogen, nitro, trifluoromethyl and trifluoromethylsulphonyl; or dichloroquinoxalinyl.

The compounds of the present invention are useful for their diuretic, saluretic and antihypertensive activity, as well as for their antithrombotic activity.

According to one embodiment of the present invention:

R is hydrogen, trifluoromethyl or alkyl of 1 to 4 carbon atoms;

$R^1$ is hydrogen or alkyl of 1 to 4 carbon atoms;

$R^2$ is alkyl of 1 to 4 carbon atoms;

$R^3$ is phenyl substituted by:
  (a) one or two of the same or different substituents selected from the group consisting of halogen, trifluoromethyl, alkyl of 1 to 4 carbon atoms, alkenyl of 2 to 4 carbon atoms, and alkoxy of 1 to 4 carbon atoms;
  (b) one substituent selected from the group consisting of alkylamino of 1 or 2 carbon atoms, dialkylamino of 1 or 2 carbon atoms in each alkyl moiety, cycloalkyl of 5 to 7 carbon atoms, cycloalkenyl of 5 to 7 carbon atoms, trifluoromethoxy, nitro, cyano, carbonamido unsubstituted or substituted by 1 or 2 alkyl moieties of 1 or 2 carbon atoms, sulphonamido unsubstituted or substituted by 1 or 2 alkyl moieties of 1 or 2 carbon atoms, $SO_n$-alkyl wherein $n$ is 0, 1 or 2, and alkyl is of 1 or 2 carbon atoms, and dialkylamino wherein the alkyl moieties together with the nitrogen atom to which they are attached form a 5- to 7-membered heterocyclic ring;
(c) one substituent selected from the group consisting of alkylamino of 1 to 4 carbon atoms, dialkylamino of 1 to 4 carbon atoms in each alkyl moiety, cycloalkyl of 5 to 7 carbon atoms, cycloalkenyl of 5 to 7 carbon atoms, trifluoromethoxy, nitro, cyano, carbonamido unsubstituted or substituted by 1 or 2 alkyl moieties of 1 to 4 carbon atoms, sulphonamido unsubstituted or substituted by 1 or 2 alkyl moieties of 1 to 4 carbon atoms, $SO_n$-alkyl wherein $n$ is 0, 1 or 2, and alkyl is of 1 to 4 carbon atoms, and dialkylamino wherein the alkyl moieties together with the nitrogen atom to which they are attached form a 5- to 7-membered heterocyclic ring, and one or two substituents selected from the group consisting of alkyl of 1 to 4 carbon atoms, alkenyl of 2 to 4 carbon atoms, alkoxy of 1 to 4 carbon atoms, halogen and trifluoromethyl; or
(d) two substituents on the phenyl moiety form a branched or unbranched saturated, partially unsaturated or unsaturated 5- to 7-membered isocyclic or heterocyclic ring wherein the heterocyclic ring has 1 or 2 hetero-atoms selected from the group consisting of oxygen and sulfur or wherein the heterocyclic ring has $SO_n$-alkyl wherein $n$ is 0, 1 or 2 and alkyl is of 1 to 4 carbon atoms as a ring member; or $R^3$ is naphthyl or pyridyl.

According to another embodiment of the present invention:

$R^3$ is phenyl substituted by 1 or 2 of the same or different substituents selected from the group consisting of chlorine, fluorine, methyl and trifluoromethyl, or linked to a tetramethylene moiety.

According to another embodiment of the present invention:

R is methyl or trifluoromethyl;
$R^1$ is hydrogen or methyl;
$R^2$ is methyl; and
$R^4$ is acetyl, trifluoroacetyl, propionyl, methoxycarbonyl, ethoxycarbonyl, thiophenecarbonyl, benzoyl unsubstituted or substituted in the phenyl moiety by methyl, methoxy, trifluoromethyl, nitro or halogen, dialkylaminocarbonyl of 1 or 2 carbon atoms in each alkyl moiety; or
$R^4$ is Z-$SO_2$ wherein Z is methyl, ethyl or phenyl unsubstituted or substituted by halogen, nitro, methyl, ethyl, trifluoromethyl or trifluoromethylsulphonyl.

According to another embodiment of the present invention:

R is hydrogen, trifluoromethyl or alkyl of 1 to 4 carbon atoms;
$R^1$ is hydrogen or alkyl of 1 to 4 carbon atoms;
$R^2$ is alkyl of 1 to 4 carbon atoms;
$R^3$ is phenyl substituted by 1 or 2 of the same or different substituents selected from the group consisting of halogen, alkyl of 1 or 2 carbon atoms and trifluoromethyl; tetramethylenephenyl; pyridylphenyl; naphthyl; or pyridyl; and
$R^4$ is $R^5$CO wherein $R^5$ is alkyl of 1 to 4 carbon atoms unsubstituted or substituted by 1, 2 or 3 fluorine or chlorine atoms, by an alkoxy moiety of 1 or 2 carbon atoms or by a mono- or dialkylamino moiety of 1 or 2 carbon atoms; alkoxy of 1 to 4 carbon atoms; thiophene; dialkylamino of 1 or 2 carbon atoms in each alkyl moiety; phenyl unsubstituted or substituted by 1 or 2 substituents selected from the group consisting of alkyl of 1 or 2 carbon atoms, alkoxy of 1 or 2 carbon atoms, trifluoromethyl, nitro or halogen; or a 5- to 7-membered heterocyclic ring unsubstituted or substituted by 1 or 2 substituents selected from the group consisting of alkyl of 1 or 2 carbon atoms, halogen and nitro; or
$R^4$ is Z-$SO_2$ wherein Z is alkyl of 1 to 4 carbon atoms; phenyl; phenyl substituted by 1 or 2 substituents selected from the group consisting of alkyl of 1 or 2 carbon atoms, halogen, nitro, trifluoromethyl, trifluoromethylsulphonyl and dichloroquinoxalinyl.

According to another embodiment of the present invention:

R is hydrogen, trifluoromethyl or alkyl of 1 to 3 carbon atoms;
$R^1$ is hydrogen, methyl or ethyl;
$R^2$ is alkyl of 1 to 3 carbon atoms;
$R^3$ is phenyl substituted by 1 or 2 substituents selected from the group consisting of methyl, fluorine, chlorine and trifluoromethyl; tetramethylenephenyl; pyridylphenyl; naphthyl; or pyridyl; and
$R^4$ is $R^5$CO wherein $R^5$ is alkyl of 1 to 4 carbon atoms unsubstituted or substituted by 1, 2 or 3 fluorine or chlorine atoms, by alkoxy of 1 or 2 carbon atoms, or by dialkylamino of 1 or 2 carbon atoms in each alkyl moiety; alkoxy of 1 or 2 carbon atoms, thiophene; dialkylamino of 1 or 2 carbon atoms in each alkyl moiety; phenyl unsubstituted or substituted by 1 or 2 substituents selected from the group consisting of alkyl of 1 or 2 carbon atoms, alkoxy of 1 or 2 carbon atoms, trifluoromethyl, nitro, chlorine and fluorine; or a heterocycle selected from the group consisting of pyrryl, thienyl, furyl, pyrazolyl, imidazolyl, thiazolyl, oxazolyl, isoxazolyl, nicotinyl, picolinyl, isonicotinyl, pyridazinyl, pyrimidinyl, pyrazinyl, piperazinyl, dihydrofuryl, tetrahydrofuryl, tetrahydropyridyl, piperidyl, tetrahydropyranyl, tetrahydrothiopyranyl, thiadiazolyl, and morpholino unsubstituted or substituted by methyl, ethyl, mono- or dichloro, fluoro or nitro; or
$R^4$ is Z-$SO_2$ wherein Z is alkyl of 1 or 2 carbon atoms; or phenyl substituted by mono- or dimethyl, mono- or dinitro, fluorine, chlorine, trifluoromethylsulphonyl; or dichloroquinoxalinyl.

According to another embodiment of the present invention:

R is methyl;
$R^1$ is hydrogen;
$R^2$ is methyl;
$R^3$ is phenyl substituted by 1 or 2 members selected from the group consisting of methyl, chlorine or fluorine; and
$R^4$ is $R^5$CO wherein $R^5$ is alkyl of 1 or 2 carbon atoms unsubstituted or substituted by 1, 2 or 3 chlorine or fluorine atoms; alkoxy of 1 or 2 carbon atoms, dimethylamino; phenyl substituted by methyl, methoxy, chlorine or trifluoromethyl; thienyl; furyl; or isoxazolyl; or
$R^4$ is Z-$SO_2$ wherein Z is methyl, phenyl substituted by methyl, or dichloroquinoxalinyl.

According to another embodiment of the present invention:

R is methyl;
$R^1$ is hydrogen;

R² is methyl;

R³ is phenyl substituted by fluorine, chlorine and methyl or dichlorine; and

R⁴ is acetyl, trifluoroacetyl, dimethylaminocarbonyl, ethoxycarbonyl, chlorobenzoyl, methylbenzoyl, trifluoromethylbenzoyl, methoxybenzoyl, thienylcarbonyl, furylcarbonyl, isoxazolylcarbonyl, methylphenylsulphonyl, methylsulphonyl or dichloroquinoxalinylsulphonyl.

The compounds of the present invention contain an asymmetric carbon atom. Thus, the racemates can be resolved into the optical antipodes and the antipodes can be administered as such or in the form of their salts.

The compounds of the present invention may be produced by reacting a pyrazolone-(5) derivative of the formula:

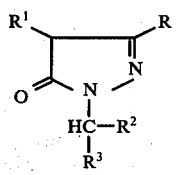

(II)

wherein

R, R¹, R² and R³ are as above defined, with the corresponding acid derivative, preferably a carboxylic acid, carbonic acid or a sulphonic acid derivative. The carboxylic acid derivative or carbonic acid derivative is of the formula:

(III)

wherein

X is a moiety which is cleaved during the course of reaction such as, for example, halogen, a 5-membered heterocyclic azole, an alkyl moiety especially lower alkyl bonded to the carbonyl carbon atom via an oxygen atom or a sulfur atom, phenyl unsubstituted or substituted by 1 or 2 nitro moieties, or an acyloxy moiety; and Y is R⁵.

The sulphonic acid derivative is of the formula:

      (IV)

wherein

Z is as above defined; and

X' is halogen.

The reaction is optionally carried out in the presence of an inert solvent and a basic auxiliary, such as an alkali metal hydroxide or carbonate or an alkaline earth metal hydroxide or carbonate or an organic base, such as triethylamine or pyridine, at a temperature of −20 to 150° C.

The preparation of the optical antipodes of the compounds according to the present invention may be carried out according to methods known from the literature (see, for example, Houben-Weyl, IV/2, pages 509 et seq.) by interaction of the compounds according to the invention with a chiral medium such as, for example, by recrystallization from an optically active solvent or by chromatography on a chiral carrier, or by reaction of the optically pure pyrazolone-(5) derivative of the formula (II) with the corresponding carboxylic acid derivative, carbonic acid derivative or sulphonic acid derivative of the formula (III) or (IV).

Depending on the nature of the starting materials used, the synthesis of the compounds according to the present invention is illustrated by the following reaction scheme, in which 3-methyl-5-acetoxy-1-(α-methyl-4-chlorobenzyl)-pyrazolone-(5) and acetyl chloride have been chosen as examples:

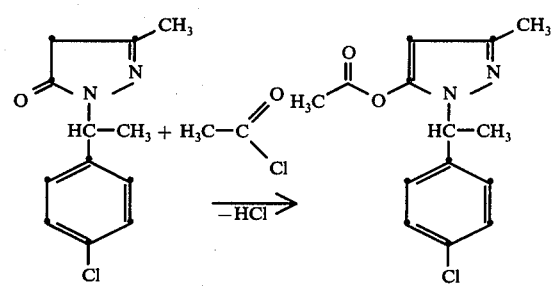

The pyrazolone-(5) derivatives of the formula (II) used as starting materials have not previously been disclosed but can be prepared according to methods known from the literature (see, for example, L. Knorr, Ber. Deutsch. Chem. Ges. 16, 2,597 (1883)), by reacting hydrazines of the formula (V) below with β-carbonyl-fatty acid derivatives of the formula (VI) below:

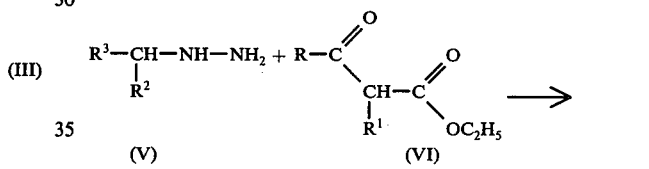

In formula (V) and (VI), R, R¹, R² and R³ are as above defined.

The compounds set forth in Table I and II below are representative of compounds of formula (II):

Table I 3-methyl-1-(α-methyl-3-fluorobenzyl)-pyrazolone-(5),
3-methyl-1-(α-methyl-4-fluorobenzyl)-pyrazolone-(5),
3-methyl-1-(α-methyl-3-chlorobenzyl)-pyrazolone-(5),
3-methyl-1-(α-methyl-4-chlorobenzyl)-pyrazolone-(5),
3-methyl-1-(α-methyl-4-bromobenzyl)-pyrazolone-(5),
3-methyl-1-(α-methyl-3,4-dichlorobenzyl)-pyrazolone-(5),
3-ethyl-1-(α-methyl-3,4-dichlorobenzyl)-pyrazolone-(5),
3-trifluoromethyl-1-(α-methyl-3,4-dichlorobenzyl)-pyrazolone-(5),
3-methyl-1-(α-methyl-3-bromo-4-chlorobenzyl)-pyrazolone-(5),
3-isopropyl-1-(α-methyl-3-bromo-4-chlorobenzyl)-pyrazolone-(5),
3-methyl-1-(α-methyl-3-trifluoromethylbenzyl)-pyrazolone-(5), 3-methyl-1-(α-methyl-4-trifluoromethylbenzyl)-pyrazolone-(5),
3-methyl-1-(α-ethyl-4-trifluoromethylbenzyl)-pyrazolone-(5),
3-methyl-1-(α-methyl-3-chloro-4-trifluoromethylbenzyl)-pyrazolone-(5),
3-methyl-1-(α-methyl-4-methylbenzyl)-pyrazolone-(5),
3-methyl-1-(α-methyl-3-chloro-4-methylbenzyl)-pyrazolone-(5),
3-methyl-1-(α-(naphthyl-2)-ethyl)-pyrazolone-(5),
3-methyl-1-(α-methyl-3,4-tetramethylenebenzyl)-pyrazolone-(5),
3-methyl-1-(α-methyl-3-methyl-4-trifluoromethylbenzyl)-pyrazolone-(5),
3-trifluoromethyl-1-(α-methyl-3-chloro-4-methylbenzyl)-pyrazolone-(5),
3-trifluoromethyl-1-(α-(naphthyl-2)-ethyl)-pyrazolone-(5),
3-trifluoromethyl-1-(α-methyl-3,4-tetramethylenebenzyl)-pyrazolone-(5),
1-(α-methyl-3,4-dichlorobenzyl)-pyrazolone-(5),
1-(α-methyl-3-chloro-4-methylbenzyl)-pyrazolone-(5),
3-methyl-1-(α-(pyridyl-3)-ethyl)-pyrazolone-(5), and
3-methyl-1-(α-(pyridyl-4)-ethyl)-pyrazolone-(5).

Table II 4-methyl-1-(α-methyl-3,4-dichlorobenzyl)-pyrazolone-(5),
4-methyl-1-(α-methyl-3-chloro-4-methylbenzyl)-pyrazolone-(5),
4-methyl-1-(α-(naphthyl-2)-ethyl)-pyrazolone-(5),
4-methyl-1-(α-methyl-3,4-tetramethylenebenzyl)-pyrazolone-(5),
3,4-dimethyl-1-(α-methyl-3-chlorobenzyl)-pyrazolone-(5),
3,4-dimethyl-1-(α-methyl-4-chlorobenzyl)-pyrazolone-(5),
3,4-dimethyl-1-(α-methyl-3,4-dichlorobenzyl)-pyrazolone-(5),
3-ethyl-4-methyl-1-(α-methyl-3,4-dichlorobenzyl)-pyrazolone-(5),
3-trifluoromethyl-4-methyl-1-(α-methyl-3,4-dichlorobenzyl)-pyrazolone-(5),
3,4-dimethyl-1-(α-methyl-4-trifluoromethylbenzyl)-pyrazolone-(5),
3,4-dimethyl-1-(α-methyl-3-chloro-4-methylbenzyl)-pyrazolone-(5),
3-trifluoromethyl-4-methyl-1-(α-methyl-3-chloro-4-methylbenzyl)-pyrazolone-(5),
3,4-dimethyl-1-(α-(naphthyl-2)-ethyl)-pyrazolone-(5),
3,4-dimethyl-1-(α-methyl-3,4-tetramethylenebenzyl)-pyrazolone-(5), and
3-trifluoromethyl-4-methyl-1-(α-methyl-3,4-tetramethylenebenzyl)-pyrazolone-(5).

As indicated above X is a moiety which is cleaved during the course of the reaction and which is suitable for acylation reactions. Suitable substituents for X include: halogen, such as fluorine, chlorine or bromine, especially chlorine, or preferably a 5-membered heterocyclic azole ring, such as imidazole, pyrazole or 1,3,4-triazole, especially imidazole, the heterocyclic ring being bonded to the carbonyl carbon atom in the formula (III) via a nitrogen atom, or preferably a moiety $R^6$ which is bonded to the carbonyl carbon atom in the formula (III) via an oxygen atom or sulfur atom and which is straight or branched chain alkyl of 1 to 4 carbon atoms or phenyl unsubstituted or substituted by one or two nitros, or an acyloxy moiety of the formula:

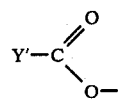

wherein
Y' is Y but need not be the same as Y in the formula (III), so that mixed anhydrides can be employed.

The starting materials of the formula (III) are known from the literature or can be prepared according to methods known from the literature (see, for example, Houben Weyl, Methoden der Organischen Chemie (Methods of Organic Chemistry), VIII, page 101 (1952), Weygand/Hilgetag, Org. Chemische Experimentierkunst (Experimental Technique in Organic Chemistry), page 246, 4th edition, 1970, published by J. A. Barth, Leipzig).

The following compounds are illustrative of those of the formula (III) which may be used in the process of the present invention: acetyl chloride, propionyl chloride, isopropionyl chloride, acetic anhydride, trifluoroacetic anhydride, propionic anhydride, butyric anhydride, β-methoxy-propionic acid chloride, phenylacetic acid chloride, phenoxyacetic acid chloride, 4-chlorophenoxyacetic acid chloride, ethoxycarbonyl acetate, phenoxycarbonyl acetate, benzoyl chloride, benzoic anhydride, thiobenzoic acid S-phenyl ester, ethoxycarbonyl benzoate, $N^1$-benzoylimidazolide, 4-chlorobenzoyl chloride, 4-fluorobenzoyl chloride, 4-trifluoromethylbenzoyl chloride, 4-trifluoromethylsulphonylbenzoyl chloride, 4-trifluoromethoxybenzoyl chloride, (4-trifluoromethylthio)-benzoyl chloride, 3,4-dichlorobenzoyl chloride, 3-chloro-4-methylbenzoyl chloride, 4-nitrobenzoyl chloride, 4-methoxybenzoyl chloride, chlorocarbonic acid ethyl ester, chlorocarbonic acid isobutyl ester, chlorocarbonic acid benzyl ester, chlorocarbonic acid β-methoxyethyl ester, chlorocarbonic acid β-phenoxyethyl ester, carbonic acid diethyl ester, carbonic acid di-n-butyl ester, pyrocarbonic acid diethyl ester, N,N-dimethylcarbamic acid chloride, N,N-diethylcarbamic acid chloride, N,N-di-n-butylcarbamic acid chloride, pyridine-(2)-carboxylic acid chloride, nicotinic acid chloride, isonicotinic acid chloride, thiophene-(2)-carboxylic acid chloride, thiophene-(3)-carboxylic acid chloride, furane-(2)-carboxylic acid chloride, furane-(3)-carboxylic acid chloride, pyrazole-(4)-carboxylic acid 4-nitrophenyl ester, pyrazole-(3)-carboxylic acid-carbonic acid monoethyl ester anhydride, 4-methylimidazole-5-carboxylic acid chloride, $N^1$-methyl-imidazole-(4)-carboxylic acid chloride, isoxazole-(3)-carboxylic acid chloride, 5-methyl-isoxazole-(3)-carboxylic acid chloride, isoxazole-(4)-carboxylic acid chloride, 5-methyl-isoxazole-(4)-carboxylic acid chloride, isoxazole-(5)-carboxylic acid chloride, 3-methyl-isoxazole-(5)-carboxylic acid chloride, isothiazole-(3)-carboxylic acid chloride, N-methylpyrrolidine-(4)-carboxylic acid chloride, ethoxycarbonyl-pyrrolidine-(2)-carboxylate, N-chlorocarbonylpiperidine, N-methyl-N'-chlorocarbonyl-piperazine and N-chlorocarbonyl-morpholine.

In formula (IV), X' is preferably chlorine.
The starting materials of formula (IV) are known from the literature or can be prepared according to methods known from the literature (see, for example, Weygand/Hilgetag, Org. Chemische Experimentierkunst (Experimental Technique in Organic Chemistry), page 691, page 704 and page 645, 4th edition, 1970, published by J. A. Barth, Leipzig).

The following compounds are illustrative of those of formula (IV) which can be used according to the process of the present invention: methanesulphonic acid chloride, ethanesulphonic acid chloride, butanesulphonic acid chloride, benzenesulphonic acid chloride, p-toluenesulphonic acid chloride, 4-chlorobenzenesulphonic acid chloride, 3-chlorobenzenesulphonic acid chloride, 4-fluorobenzenesulphonic acid chloride, 3,4-dichlorobenzenesulphonic acid chloride and 3-chloro-4-methylbenzenesulphonic acid chloride.

If a diluent is used in the process of the invention, it may be any inert solvent; preferred examples include hydrocarbons (such as benzene, toluene and xylene), halogenated hydrocarbons (such as methylene chloride, chloroform, carbon tetrachloride and chlorobenzene), ethers (such as tetrahydrofuran, dioxan and glycol dimethyl ether), amides (such as dimethylformamide, dimethylacetamide, N-methylpyrrolidone and hexamethylphosphoric acid triamide), sulphoxides (such as dimethylsulphoxide), sulphones (such as sulpholane) and bases, such as pyridine, picoline, collidine, lutidine and quinoline.

Inorganic and organic bases can be used as basic auxiliaries. Preferred examples include alkali metal hydroxides and alkali metal carbonates, such as sodium hydroxide or potassium carbonate, and tertiary amines, such as triethylamine or pyridine.

The reaction can be carried out within a wide temperature range. In general, the reaction is carried out at −10° to 150° C., preferably 0 to 100° C. The reaction may be carried out under normal pressure but can also be carried out in closed vessels at a higher pressure.

In carrying out the process according to the invention, 1 mol of the pyrazolone-(5) derivative may be reacted with 1 to 5 mols of the compound of formula (III) in an inert diluent, optionally in the presence of an equimolar amount of a basic auxiliary, such as triethylamine or pyridine. The compounds according to the invention, which after removal of the diluent are in most cases obtained in a crystalline form, can in such cases easily be purified by recrystallisation from a suitable solvent.

The following compounds set forth in Tables III and IV below are illustrative of the pyrazoles according to the present invention:

TABLE III 5-acetoxy-3-trifluoromethyl-1-(α-methyl-3,4-dichlorobenzyl)-pyrazole,
5-acetoxy-3-methyl-1-(α-methyl-3-chloro-4-methylbenzyl)-pyrazole,
5-acetoxy-3,4-dimethyl-1-(α-methyl-3-chloro-4-methylbenzyl)-pyrazole,
5-acetoxy-3,4-dimethyl-1-(α-methyl-3,4-dichlorobenzyl)-pyrazole,
5-acetoxy-3-methyl-1-(α-naphthyl-(2)-ethyl)-pyrazole,
5-acetoxy-4-methyl-1-(α-methyl-3,4-dichlorobenzyl)-pyrazole,
5-acetoxy-3-methyl-1-(α-methyl-4-fluorobenzyl)-pyrazole,
5-acetoxy-3,4-dimethyl-1-(α-pyridyl-(3)-ethylbenzyl)-pyrazole,
5-acetoxy-3,4-dimethyl-1-(α-methyl-3,4-di-trifluoromethylbenzyl)-pyrazole,
5-propionyloxy-3-methyl-1-(α-propyl-3,4-dichlorobenzyl)-pyrazole,
5-propionyloxy-3-methyl-1-(α-methyl-3,4-dichlorobenzyl)-pyrazole,
5-propionyloxy-3,4-dimethyl-1-(α-methyl-3-chloro-4methylbenzyl)-pyrazole,
5-propionyloxy-3-isopropyl-1-(α-methyl-3,4-dichlorobenzyl)-pyrazole,
5-n-butyryloxy-3-methyl-1-(α-methyl-3,4-dichlorobenzyl)-pyrazole,
5-trimethylacetoxy-3-methyl-1-(α-methyl-3-chloro-4-methylbenzyl)-pyrazole,
5-isovaleryloxy-3-methyl-1-(α-methyl-3,4-difluorobenzyl)-pyrazole,
5-trifluoroacetoxy-3-methyl-1-(α-methyl-3,4-dichlorobenzyl)-pyrazole,
5-trifluoroacetoxy-3,4-dimethyl-1-(α-methyl-3,4-dichlorobenzyl)-pyrazole,
5-trifluoroacetoxy-3-methyl-1-(α-methyl-3-chloro-4-methylbenzyl)-pyrazole,
5-trifluoroacetoxy-3,4-dimethyl-1-(α-methyl-3-chloro-4-methylbenzyl)-pyrazole,
5-trifluoroacetoxy-3-methyl-1-(α-methyl-4-fluorobenzyl)-pyrazole,
5-trifluoroacetoxy-3-methyl-1-(α-methyl-4-trifluoromethylbenzyl)-pyrazole,
5-trifluoroacetoxy-3,4-dimethyl-1-(α-methyl-3,4-ditrifluoromethylbenzyl)-pyrazole,
5-chloroacetoxy-3-methyl-1-(α-methyl-3,4-dichlorobenzyl)-pyrazole,
5-chloroacetoxy-3-methyl-1-(α-methyl-3-chloro-4-methylbenzyl)-pyrazole,
5-chloroacetoxy-3-methyl-1-(α-methyl-4-chloro-3-methylbenzyl)-pyrazole,
5-dichloroacetoxy-3-methyl-1-(α-methyl-3,4-dichlorobenzyl)-pyrazole,
5-dichloroacetoxy-3-methyl-1-(α-methyl-3-chloro-4-methylbenzyl)-pyrazole,
5-dichloroacetoxy-3,4-dimethyl-1-(α-methyl-3,4-dichlorobenzyl)-pyrazole,
5-trichloroacetoxy-3-methyl-1-(α-methyl-3,4-dichlorobenzyl)-pyrazole,
5-(3-chloropropionyloxy)-3-methyl-1-(α-methyl-3,4-dichlorobenzyl)-pyrazole,
5-(2-methoxyacetoxy)-3-methyl-1-(α-methyl-3,4-dichlorobenzyl)-pyrazole,
5-(2-methoxyacetoxy)-3-methyl-1-(α-methyl-3-chloro-4-methylbenzyl)-pyrazole,
5-(2-ethoxyacetoxy)-3-methyl-1-(α-methyl-3,4-dichlorobenzyl)-pyrazole,
5-(2-dimethylaminoacetoxy)-3-methyl-1-(α-methyl-3-chloro-4-methylbenzyl)-pyrazole,
5-(2-fluorobenzoyloxy)-3,4-dimethyl-1-(α-methyl-3,4-dichlorobenzyl)-pyrazole,
5-(3-fluorobenzoyloxy)-3-methyl-1-(α-ethyl-3,4-difluorobenzyl)-pyrazole,
5-(4-fluorobenzoyloxy)-3-methyl-1-(α-methyl-4-fluorobenzyl)-pyrazole,
5-(4-nitrobenzoyloxy)-3-methyl-1-(α-methyl-4-chlorobenzyl)-pyrazole,
5-(4-nitrobenzoyloxy)-3-methyl-1-(α-methyl-3,4-dichlorobenzyl)-pyrazole,
5-(3,4-dinitrobenzoyloxy)-3-methyl-1-(α-methyl-3-chloro-4-methylbenzyl)-pyrazole,
5-(3-methylbenzoyloxy)-3-methyl-1-(α-methyl-3-chlorobenzyl)-pyrazole,
5-(3,4-dimethylbenzoyloxy)-3-methyl-1-(α-methyl-3,4-dichlorobenzyl)-pyrazole, 5-(3-chlorobenzoyloxy)-3-methyl-1-(α-methyl-3-trifluoromethylbenzyl)-pyrazole,
5-(3,4-dichlorobenzoyloxy)-3,4-dimethyl-1-(α-methyl-3,4-dimethylbenzyl)-pyrazole,
5-(3,5-difluorobenzoyloxy)-3-methyl-1-(α-methyl-3,4-dichlorobenzyl)-pyrazole,
5-(3,5-dinitrobenzoyloxy)-3-methyl-1-(α-methyl-3-methyl-4-chlorobenzyl)-pyrazole,
5-(3,4-di-trifluoromethylbenzoyloxy-3-methyl-1-(α-methyl-3,4-dichlorobenzyl)-pyrazole,
5-(4-trifluoromethylsulphonylbenzoyloxy)-3-methyl-1-(α-naphthyl-(2)-ethyl)-pyrazole,
5-(4-trifluoromethoxybenzoyloxy)-3-methyl-1-(α-methyl-3,4-dichlorobenzyl)-pyrazole,
5-(pyrryl-(2)-carbonyloxy)-3-methyl-1-(α-methyl-3,4-dichlorobenzyl)-pyrazole,
5-(pyrryl-(3)-carbonyloxy)-3,4-dimethyl-1-(α-methyl-3-chloro-4-methylbenzyl)pyrazole,
5-(thienyl-(2)-carbonyloxy)-3-methyl-1-(α-pyridyl-(2)-ethyl)-pyrazole,
5-(thienyl-(3)-carbonyloxy)-3-methyl-1-(α-methyl-3,4-difluorobenzyl)-pyrazole,
5-(3-fluorothienyl-(2)-carbonyloxy)-3-methyl-1-(α-naphthyl-(2)-ethyl)-pyrazole,
5-(4-fluorothienyl-(2)-carbonyloxy)-3,4-dimethyl-1-(α-methyl-4-chlorobenzyl)-pyrazole,
5-(5-fluorothienyl-(2)-carbonyloxy)-3-methyl-1-(α-methyl-3,4-dichlorobenzyl)-pyrazole,
5-(furyl-(2)-carbonyloxy)-3-methyl-1-(α-methyl-3,4-dichlorobenzyl)-pyrazole,
5-(furyl-(3)-carbonyloxy)-3-methyl-1-(α-methyl-4-fluorobenzyl)-pyrazole,
5-(4-fluorofuryl-(2)-carbonyloxy)-3-methyl-1-(α-methyl-3,4-dichlorobenzyl)-pyrazole,
5-(pyrazolyl-(3)-carbonyloxy)-3-methyl-1-(α-methyl-3,4-dichlorobenzyl)-pyrazole,
5-(pyrazolyl-(4)-carbonyloxy)-3,4-dimethyl-1-(α-methyl-4-chlorobenzyl)-pyrazole,
5-(4-methylpyrazolyl-(3)-carbonyloxy)-3-methyl-1-(α-pyridyl-(3)-ethyl)-pyrazole,
5-(5-methylpyrazolyl-(3)-carbonyloxy)-3-methyl-1-(α-methyl-3,4-dichlorobenzyl)-pyrazole,
5-(4-methylimidazolyl-(2)-carbonyloxy)-3-ethyl-1-(α-methyl-3,4-dichlorobenzyl)-pyrazole,
5-(4-methylimidazolyl-(3)-carbonyloxy)-3-methyl-1-(α-methyl-3,4-dichlorobenzyl)-pyrazole,
5-(2-methylimidazolyl-(4)-carbonyloxy)-3-methyl-1-(α-methyl-3,4-di-trifluoromethylbenzyl)-pyrazole,
5-(imidazolyl-(2)-carbonyloxy)-4-methyl-1-(α-methyl-3,4-dichlorobenzyl)pyrazole,
5-(imidazolyl-(4)-carbonyloxy)-4-ethyl-1-(α-methyl-3,4-dimethylbenzyl)-pyrazole,
5-(thiazolyl-(2)-carbonyloxy)-3-methyl-1-(α-methyl-3,4-dichlorobenzyl)-pyrazole,
5-(thiazolyl-(4)carbonyloxy)-3,4-dimethyl-1-(α-methyl-3-chlorobenzyl)-pyrazole,
5-(thiazolyl-(5)-carbonyloxy)-3-methyl-1-(α-pyridyl-(3)-ethyl)-pyrazole,
5-(5-nitrothiazolyl-(2)-carbonyloxy)-3-methyl-1-(α-naphthyl-(2)-ethyl)-pyrazole,
5-(oxazolyl-(2)-carbonyloxy)-3-methyl-1-(α-methyl-3,4-dichlorobenzyl)-pyrazole,
5-(oxazolyl-(4)-carbonyloxy)-3,4-dimethyl-1-(α-methyl-3,4-dichlorobenzyl)-pyrazole,
5-(oxazolyl-(5)-carbonyloxy)-3-methyl-1-(α-methyl-4-fluorobenzyl)-pyrazole,
5-(isoxazolyl-(3)-carbonyloxy)-3-methyl-1-(α-methyl-3,4-dichlorobenzyl)-pyrazole,
5-(isoxazolyl-(4)-carbonyloxy)-3,4-dimethyl-1-(α-methyl-4-chlorobenzyl)-pyrazole,
5-(isoxazolyl-(5)-carbonyloxy)-3-methyl-1-(α-methyl-3-chlorobenzyl)-pyrazole,
5-(5-methylisoxazolyl-(3)-carbonyloxy)-3-methyl-1-(α-methyl-3,4-dichlorobenzyl)-pyrazole,
5-(5-methylisoxazolyl-(3)-carbonyloxy)-3-methyl-1-(α-methyl-3-chloro-4-methylbenzyl)-pyrazole,
5-(4-methylisoxazolyl-(3)-carbonyloxy)-3-methyl-1-(α-methyl-3,4-dichlorobenzyl)-pyrazole,
5-(3-fluoropicolinoyloxy)-3-methyl-1-(α-methyl-3,4-dichlorobenzyl)-pyrazole,
5-(4-fluoropicolinoyloxy)-3,4-dimethyl-1-(α-methyl-3,4-dichlorobenzyl)-pyrazole,
5-(5-fluoropicolinoyloxy)-3-methyl-1-(α-methyl-3,4-difluorobenzyl)-pyrazole,
5-(6-fluoropicolinoyloxy)-3-methyl-1-(α-methyl-3,4-dichlorobenzyl)-pyrazole,
5-(picolinoyloxy)-4-methyl-1-(α-methyl-3,4-dichlorobenzyl)-pyrazole,
5-(nicotinoyloxy)-3-methyl-1-(α-methyl-3,4-difluorobenzyl)-pyrazole,
5-(2-fluoronicotinoyloxy)-3-methyl-1-(α-ethyl-4-chlorobenzyl)-pyrazole,
5-(4-fluoronicothinoyloxy)-3,4-dimethyl-1-(α-methyl-3,4-dichlorobenzyl)-pyrazole,
5-(5-fluoronicotinoyloxy)-3-methyl-1-(α-methyl-4-chlorobenzyl)-pyrazole,
5-(6-fluoronicotinoyloxy)-3-methyl-1-(α-methyl-3,4-dichlorobenzyl)-pyrazole, 5-(2-chloronicotinoyloxy)-3-methyl-1-(α-methyl-3,4-dichlorobenzyl)-pyrazole,
5-(4-chloronicotinoyloxy)-3-methyl-1-(α-methyl-3,4-dichlorobenzyl)-pyrazole,
5-(4-chloronicotinoyloxy)-3,4-dimethyl-1-(α-methyl-3,4-dichlorobenzyl)-pyrazole,
5-(4-chloronicotinoyloxy)-3-methyl-1-(α-methyl-3,4-difluorobenzyl)-pyrazole,
5-(5-chloronicotinoyloxy)-3-methyl-1-(α-methyl-3,4-dichlorobenzyl)-pyrazole,
5-(6-chloronicotinoyloxy)-3-methyl-1-(α-methyl-3,4-dichlorobenzyl)-pyrazole,
5-(isonicotinoyloxy)-3-methyl-1-(α-methyl-3,4-dichlorobenzyl)-pyrazole,
5-(2,6-dichloroisonicotinoyloxy)-3-methyl-1-(α-methyl-3,4-dichlorobenzyl)-pyrazole,
5-(2,6-dichloroisonicotinoyloxy)-3,4-dimethyl-1-(α-methyl-3,4-dichlorobenzyl)-pyrazole,
5-(pyridazinyl-(3)-carbonyloxy)-3-methyl-1-(α-methyl-3,4-dichlorobenzyl)-pyrazole,
5-(pyridazinyl-(4)-carbonyloxy)-3-methyl-1-(α-methyl-4-fluorobenzyl)-pyrazole,
5-(pyrimidinyl-(2)-carbonyloxy)-3-methyl-1-(α-methyl-3,4-dichlorobenzyl)-pyrazole,
5-(pyrimidinyl-(4)-carbonyloxy)-3-methyl-1-(α-methyl-4-fluorobenzyl)-pyrazole,
5-(pyrimidinyl-(5)-carbonyloxy)-3-methyl-1-(α-methyl-4-chlorobenzyl)-pyrazole,
5-(pyrazinyl-(2)-carbonyloxy)-3-methyl-1-(α-methyl-3,4-dichlorobenzyl)-pyrazole,
5-(4-methylpiperazinyl-(1)-carbonyloxy)-3-methyl-1-(α-methyl-3,4-dichlorobenzyl)-pyrazole,
5-(dihydrofuryl-(2)-carbonyloxy)-3-methyl-1-(α-methyl-3,4-dichlorobenzyl)-pyrazole, 5-(tetrahydrofuryl-(2)-carbonyloxy)-3,4-dimethyl-1-(α-methyl-3,4-dichlorobenzyl)-pyrazole,
5-(tetrahydrofuryl-(3)-carbonyloxy)-3-methyl-1-(α-methyl-4-fluorobenzyl)pyrazole, 5-(1-methyl-1,4,5,6-tetrahydropyridyl-(3)-carbonyloxy)-3-methyl-1-(α-methyl-3,4-dichlorobenzyl)-pyrazole,
5-(1-methylpiperidyl-(2)-carbonyloxy)-3-methyl-1-(α-methyl-3,4-dichlorobenzyl)-pyrazole,
5-(1-methylpiperidyl-(3)-carbonyloxy)-3-methyl-1-(α-methyl-4-chlorobenzyl)-pyrazole,
5-(1-methylpiperidyl-(4)-carbonyloxy)-3-methyl-1-(α-methyl-4-fluorobenzyl)-pyrazole,
5-(1-ethylpiperidyl-(2)-carbonyloxy)-3,4-dimethyl-1-(α-methyl-3,4-dichlorobenzyl)-pyrazole,
5-(1-ethylpiperidyl-(3)-carbonyloxy)-3-methyl-1-(α-methyl-4-chlorobenzyl)-pyrazole,
5-(1-ethylpiperidyl-(4)-carbonyloxy)-3-methyl-1-(α-methyl-3,4-dichlorobenzyl)-pyrazole,
5-(tetrahydropyranyl-(2)-carbonyloxy)-3-methyl-1-(α-methyl-3,4-dichlorobenzyl)-pyrazole,
5-(tetrahydrothiopyranyl-(2)-carbonyloxy)-3-methyl-1-(α-methyl-3,4-dichlorobenzyl)-pyrazole,
5-(tetrahydrothiopyranyl-(3)-carbonyloxy)-3-methyl-1-(α-methyl-3,4-difluorobenzyl)-pyrazole,
5-(tetrahydrothiopyranyl-(4)-carbonyloxy)-3-methyl-1-(α-methyl-3-chloro-4-methylbenzyl)-pyrazole,
5-(1,2,3-thiadiazolyl-(4)-carbonyloxy)-3-methyl-1-(α-methyl-3,4-dichlorobenzyl)-pyrazole,
5-(morpholinocarbonyloxy)-3-methyl-1-(α-methyl-3,4-dichlorobenzyl)-pyrazole,
5-(2-fluorophenylsulphonyloxy)-3,4-dimethyl-1-(α-methyl-3,4-dichlorobenzyl)-pyrazole,
5-(4-fluorophenylsulphonyloxy)-3-methyl-1-(α-methyl-4-fluorobenzyl)-pyrazole,
5-(4-nitrophenylsulphonyloxy)-3-methyl-1-(α-methyl-3,4-dichlorobenzyl)-pyrazole,
5-(3,4-dinitrophenylsulphonyloxy)-3-methyl-1-(α-methyl-3-chloro-4-methylbenzyl)-pyrazole,
5-(3-methylphenylsulphonyloxy)-3-methyl-1-(α-methyl-3-chlorobenzyl)-pyrazole,
5-(3,4-dimethylphenylsulphonyloxy)-3-methyl-1-(α-methyl-3,4-dichlorobenzyl)-pyrazole,
5-(3-chlorophenylsulphonyloxy)-3-methyl-1-(α-methyl-3-trifluoromethylbenzyl)-pyrazole,
5-(4-trifluoromethylsulphonylphenylsulphonyloxy)-3-methyl-1-(α-naphthyl-(2)-ethyl)-pyrazole, and
5-(ethoxycarbonyloxy)-3-methyl-1-(pyridyl-(3)-ethyl)-pyrazole.
5-acetoxy-3-methyl-1-(α-methyl-3,4-tetramethylenebenzyl)-pyrazole,
5-acetoxy-3,4-dimethyl-1-(α-methyl-3,4-tetramethylenebenzyl)-pyrazole,
5-propionyloxy-3-methyl-1-(α-methyl-3,4-tetramethylenebenzyl)-pyrazole,
5-propionyloxy-3,4-dimethyl-1-(α-methyl-3,4-tetramethylenebenzyl)-pyrazole,
5-chloroacetoxy-3-methyl-1-(α-methyl-3,4-tetramethylenebenzyl)-pyrazole,
5-(3-fluorobenzoyloxy)-3-methyl-1-(α-methyl-3,4-tetramethylenebenzyl)-pyrazole,
5-(3,4-dichlorobenzoyloxy)-3-methyl-1-(α-methyl-3,4-tetramethylenebenzyl)-pyrazole,
5-(3,4-dichlorobenzoyloxy)-3,4-dimethyl-1-(α-methyl-3,4-tetramethylenebenzyl)-pyrazole,
5-chloroacetoxy-3-methyl-1-(α-methyl-3,4-tetramethylenebenzyl)-pyrazole,
5-(3-fluorobenzoyloxy)-3-methyl-1-(α-methyl-3,4-tetramethylenebenzyl)-pyrazole,
5-(3,4-dichlorobenzoyloxy)-3-methyl-1-(α-methyl-3,4-tetramethylenebenzyl)-pyrazole,
5-(3,4-dichlorobenzoyloxy)-3,4-dimethyl-1-(α-methyl-3,4-tetramethylenebenzyl)-pyrazole,
5-(3-fluorophenylsulphonyloxy)-3-methyl-1-(α-methyl-3,4-tetramethylenebenzyl)-pyrazole, and
5-(4-fluorophenylsulphonyloxy)-3-methyl-1-(α-methyl-3,4-tetramethylenebenzyl)-pyrazole.

The compounds of the present invention can be administered either orally or parenterally to increase the elimination of water and salt and, therefore, can be used for the treatment of oedematous and hypertonic conditions and for washing out toxic substances. In addition, the compounds can be employed in the case of acute kidney failure.

In general, they are of use in conditions involving thromboses and conditions which are favorably influenced by changing the water-electrolyte balance.

The pharmaceutical compositions of the present invention contain a major or minor amount e.g. 0.1% to 99.5%, preferably 0.5% to 90% of at least one pyrazole derivative as above defined in combination with a pharmaceutically acceptable nontoxic, indert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally for parenteral administration the dosage will be from 0.01 to 50 mg/kg, preferably 0.1 to 10 mg/kg, of body weight per day, and for oral administration the dosage will be from 0.1 to 500 mg/kg, preferably 0.5 to 100 mg/kg, of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

While the routes of administration include, oral, parenteral (i.e., intramuscular, intraperitoneal, and intravenous) and rectal, parenteral and oral administrations are particularly preferred.

The following formulation is illustrative of the pharmaceutical compositions of the present invention:

200 g of 5-acetoxy-3-methyl-1-($\alpha$-methyl-3,4-dichlorobenzyl)-pyrazole were ground to a powder and mixed with 300 g of lactose and 200 g of potato starch, and after moistening with an aqueous gelatine solution and the mixture was granulated by passing through a sieve.

After drying, 60 g of talc and 5 g of sodium laurylsulphate were added. Approximately 10,000 tablets, each containing 20 mg of active compound, were pressed from this mixture.

To demonstrate the diuretic and saluretic effect of the compounds according to the invention and its course with time, 5-acetoxy-3-methyl-1-($\alpha$-methyl-3,4-dichlorobenzyl)-5-pyrazole, whose preparation is described in Example 1, was administered to dogs as described below. (Comparable properties were shown by other compounds of the invention.)

Diuresis experiment with dogs

Beagle bitches were used for the diuresis experiments. After appropriate pretreatment, the animals were given the test preparation, administered orally, in 1 ml/kg of 0.1% strength tragacanth mucilage. The urine was subsequently collected in periods of 30 minutes each. The change in the rates of elimination was detected by comparison with control animals which were given 1 ml/kg of tragacanth mucilage without test substance. The elimination of the electrolytes was calculated from the volume of urine and the measured electrolyte concentration. Sodium, potassium, chloride and bicarbonate were determined in accordance with customary chemical and physico-chemical methods of analysis.

As an example of the extremely strong saluretic and diuretic effect, Table A shows an experiment with 5-acetoxy-3-methyl-1-($\alpha$-methyl-3,4-dichlorobenzyl)-pyrazole which was administered orally in a dosage of 3 mg/kg. The effect was most intense in the first hour after administration. In this period the elimination of $Na^+$ and $Cl^-$ increased more than 20-fold compared to the control! The effect then slowly subsided up to the 3rd hour but even at the end of the experiment the rates of elimination were throughout still distinctly above the control values. Over the entire period of the experiment, the sodium ions eliminated, 7,251 $\mu$-equivalent/kg/3 hours, were substantially more than in the case of the control animals (828 $\mu$equivalent/kg/3 hours). The elimination of $K^+$ and $HCO_3^-$ was less strongly influenced. The values in Table A for the elimination of $Na^+$, $K^+$, $Cl^-$ and $HCO_3^-$ are expressed as $\mu$equivalent/kg/30 minutes except in the last column where they are expressed as $\mu$equivalents/kg/3 hours; for the elimination of $H_2O$ they involve ml rather than $\mu$equivalents.

Table A

Control experiments/mean value from 14 animals

Minutes after administration

Table A-continued

| | Control experiments/mean value from 14 animals | | | | | | |
|---|---|---|---|---|---|---|---|
| | 1–30 | 31–60 | 61–90 | 91–120 | 121–150 | 151–180 | 1–180 |
| Elimination of $Na^+$ | 58 | 72 | 78 | 128 | 222 | 265 | 828 |
| Elimination of $K^+$ | 70 | 60 | 58 | 62 | 74 | 67 | 390 |
| Elimination of $Cl^-$ | 72 | 110 | 118 | 152 | 233 | 248 | 933 |
| Elimination of $HCO_3^-$ | 36 | 19 | 15 | 27 | 43 | 47 | 186 |
| Elimination of $H_2O$ | 5.9 | 5.3 | 3.4 | 3.0 | 3.5 | 2.8 | 24.0 |

Elimination after 3 mg/kg of 5-acetoxy-3-methyl-1-(α-methyl-3,4-dichlorobenzyl)-pyrazole, given orally

| Mean value from 4 animals | Minutes after administration | | | | | | |
|---|---|---|---|---|---|---|---|
| | 1–30 | 31–60 | 61–90 | 91–120 | 121–150 | 151–180 | 1–180 |
| Elimination of $Na^+$ | 1,594 | 1,943 | 1,338 | 911 | 931 | 534 | 7,251 |
| Elimination of $K^+$ | 294 | 305 | 249 | 216 | 216 | 182 | 1,460 |
| Elimination of $Cl^-$ | 1,788 | 2,189 | 1,561 | 1,080 | 1,030 | 606 | 8,254 |
| Elimination of $HCO_3^-$ | 38 | 32 | 22 | 39 | 80 | 63 | 273 |
| Elimination of $H_2O$ | 18.4 | 18.7 | 11.4 | 7.5 | 7.2 | 4.1 | 67.4 |

The following non-limitative examples more particularly illustrate the present invention:

EXAMPLE 1

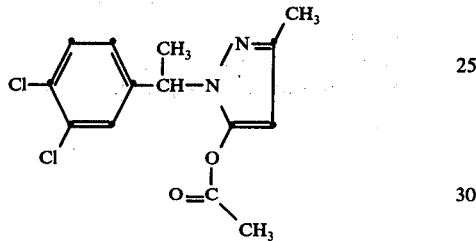

18.9 g of 3-methyl-1-(α-methyl-3,4-dichlorobenzyl)-pyrazolone-(5) were dissolved in 100 ml of acetic anhydride. After adding 8 g of sodium acetate, the reaction mixture was heated for 2 hours under reflux. After working up, the reaction product was obtained in a crystalline form through trituration with petroleum ether. It was recrystallized three times from ether.

Melting point: 46°–48° C.; Yield: 4.7 g (22%)

EXAMPLE 2

In a manner analogous to that described above in Example 1, the following end product was produced from the starting materials set forth:

Starting materials

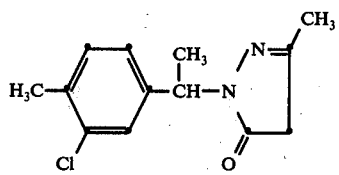

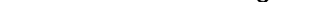

End product

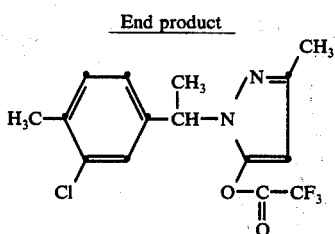

-continued
Yield: 32%

EXAMPLE 3

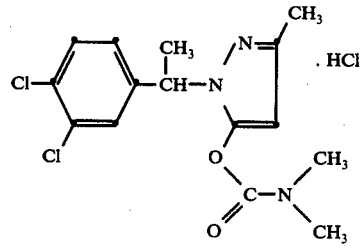

13.5 g of 3-methyl-1-(α-methyl-3,4-dichlorobenzyl)-pyrazolone-(5), 8.4 g of $K_2CO_3$ and 0.5 g of KI in 100 ml of absolute benzene were mixed with 5.8 g of dimethylcarbamic acid chloride while stirring. After heating for 15 hours under reflux, the insoluble material was filtered off. The reaction solution was concentrated and a solution of HCl in ether was added. The crystalline crude product thereby produced was recrystallized from methanol.

Melting point: 138°–140° C.; yield: 8.5 g (45%)

In a manner analogous to that described above in Example 3, the following end product was produced from the starting materials set forth:

Starting materials

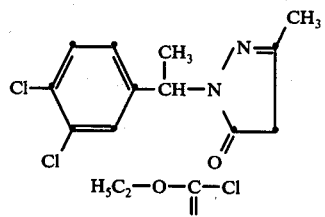

End product

-continued

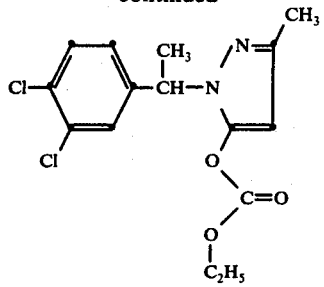

Yield: 30%
Oil

EXAMPLE 5

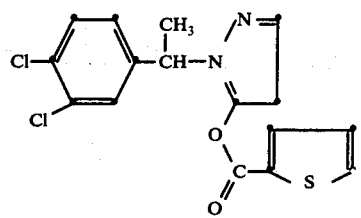

8.2 g of 2-thiophenecarboxylic acid chloride were added dropwise to 13.5 g of 3-methyl-1-(α-methyl-3,4-dichlorobenzyl)-pyrazolone-(5) and 8.25 ml of triethylamine, while stirring. After the exothermic reaction had ended, the reaction mixture was heated under reflux for 3 hours. After working up, the reaction product was obtained in a crystalline form by trituration with ether. It was recrystallized from ethanol.
Melting point: 63°–65° C.; yield: 12.7 g (67%)

EXAMPLES 6–11

In a manner analogous to that described above in Example 5, the following end products were produced from the starting materials set forth:

| Example No. | Starting materials | End product | Yield | Melting point |
|---|---|---|---|---|
| 6 | | | 73 % | 109–111° C (ethanol) |
| 7 | | | 61 % | 112–114° C (ethanol) |
| 8 | | | 82 % | 109–111° C (ethanol) |

| Example No. | Starting materials | End product | Yield | Melting point |
|---|---|---|---|---|
| 9 | | | 50% | ethanol |
| 10 | | | 60% | 77–79° C (methanol) |
| 11 | | | 45% | 64–66° C (ether) |

EXAMPLE 12

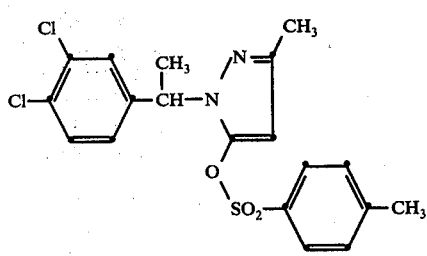

9.5 g of p-toluenesulphochloride were added to 13.5 g of 3-methyl-1-(α-methyl-3,4-dichlorobenzyl)-pyrazolone-(5) in 100 ml of absolute pyridine. The mixture was then heated for 2 hours under reflux and the solvent wad distilled off in vacuo. The resulting crude product was recrystallized twice from ethanol.

Melting point: 111°–113° C.
Yield: 15.5 g (74% of theory).

In a manner analogous to that described above in Example 12, the following end products were produced from the starting materials set forth:

EXAMPLE 13

Starting materials

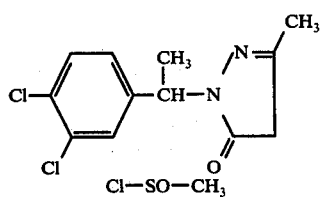

End product

-continued

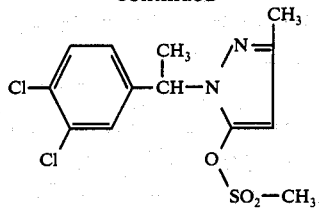

Melting point: 83°-85° C. (ether)
Yield: 59%

EXAMPLE 14

Starting materials

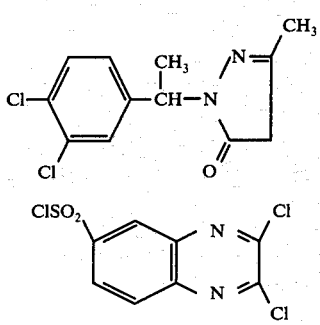

End product

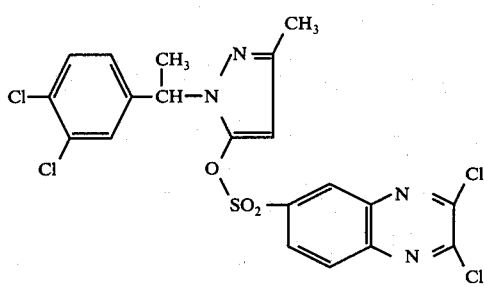

Melting point: 139°-141° C. (methanol)
Yield: 50%

What is claimed is:

1. A compound of the formula:

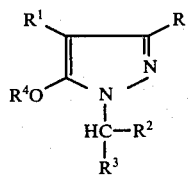

or a pharmaceutically acceptable nontoxic salt thereof wherein
R is hydrogen or lower alkyl;
$R^1$ is hydrogen or lower alkyl;
$R^2$ is lower alkyl;
$R^3$ is phenyl substituted by:
(a) one or two of the same or different substituents selected from the group consisting of halogen, trifluromethyl, alkyl of 1 to 8 carbon atoms, alkenyl of 2 to 8 carbon atoms, and alkoxy of 1 to 6 carbon atoms;
(b) one substituent selected from the group consisting of cycloalkyl of 5 to 7 carbon atoms, cycloalkenyl of 5 to 7 carbon atoms and nitro; or
(c) one substituent selected from the group consisting of cycloalkyl of 5 to 7 carbon atoms, cycloalkenyl of 5 to 7 carbon atoms and nitro and one or two substituents selected from the group consisting of alkyl of 1 to 8 carbon atoms, alkenyl of 2 to 8 carbon atoms, alkoxy of 1 to 6 carbon atoms, halogen and trifluoromethyl; or
$R^3$ is naphthyl; and
$R^4$ is $R^5CO$ wherein $R^5$ is phenyl unsubstituted or substituted by 1 or 2 members selected from the group consisting of alkyl of 1 to 4 carbon atoms, alkoxy of 1 to 4 carbon atoms, trifluoromethyl, nitro and halogen.

2. A compound according to claim 1 wherein $R^3$ is phenyl substituted by:
(a) one or two of the same or different substituents selected from the group consisting of halogen, trifluoromethyl, alkyl of 1 to 8 carbon atoms, alkenyl of 2 to 8 carbon atoms, and alkoxy of 1 to 6 carbon atoms;
(b) one substituent selected from the group consisting of cycloalkyl of 5 to 7 carbon atoms, cycloalkenyl of 5 to 7 carbon atoms and nitro; or
(c) one substituent selected from the group consisting of cycloalkyl of 5 to 7 carbon atoms, cycloalkenyl of 5 to 7 carbon atoms and nitro and one or two substituents selected from the group consisting of alkyl of 1 to 8 carbon atoms, alkenyl of 2 to 8 carbon atoms, alkoxy of 1 to 6 carbon atoms, halogen and trifluoromethyl; and
$R^4$ is $R^5CO$ wherein $R^5$ is phenyl unsubstituted or substituted by one or two members selected from the group consisting of alkyl of 1 to 4 carbon atoms, alkoxy of 1 to 4 carbon atoms, trifluoromethyl, nitro, and halogen.

3. A compound according to claim 1 wherein
R is hydrogen or alkyl of 1 to 4 carbon atoms;
$R^1$ is hydrogen or alkyl of 1 to 4 carbon atoms;
$R^3$ is phenyl substituted by:
(a) one or two of the same or different substituents selected from the group consisting of halogen, trifluoromethyl, alkyl of 1 to 4 carbon atoms, alkenyl of 2 to 4 carbon atoms, and alkoxy of 1 to 4 carbon atoms;
(b) one substituent selected from the group consisting of cycloalkyl of 5 to 7 carbon atoms, cycloalkenyl of 5 to 7 carbon atoms and nitro; or
(c) one substituent selected from the group consisting of cycloalkyl of 5 to 7 carbon atoms, cycloalkenyl of 5 to 7 carbon atoms and nitro, and one or two substituents selected from the group consisting of alkyl of 1 to 4 carbon atoms, alkenyl of 2 to 4 carbon atoms, alkoxy of 1 to 4 carbon atoms, halogen and trifluoromethyl; or
$R^3$ is naphthyl.

4. A compound according to claim 3 wherein
$R^3$ is phenyl substituted by 1 or 2 of the same or different substituents selected from the group consisting of chlorine, fluorine, methyl and trifluoromethyl.

5. A compound according to claim 4 wherein
R is methyl;
$R^1$ is hydrogen or methyl;
$R^2$ is methyl;
$R^3$ is phenyl substituted by 1 or 2 of the same or different substituents selected from the group consisting of chlorine, fluorine, methyl and trifluoromethyl; and R⁴ is benzoyl unsubstituted or substituted in the phenyl moiety by methyl, methoxy, trifluoromethyl, nitro or halogen.

6. A compound according to claim 1 wherein
R is hydrogen or alkyl of 1 to 4 carbon atoms;
R¹ is hydrogen or alkyl of 1 to 4 carbon atoms;
R² is alkyl of 1 to 4 carbon atoms;
R³ is phenyl substituted by 1 or 2 of the same or different substituents selected from the group consisting of halogen, alkyl of 1 or 2 carbon atoms and trifluoromethyl; or naphthyl; and
R⁴ is R⁵CO wherein R⁵ is phenyl unsubstituted or substituted by 1 or 2 substituents selected from the group consisting of alkyl of 1 or 2 carbon atoms, trifluoromethyl, nitro or halogen;

7. A compound according to claim 1 wherein
R is hydrogen or alkyl of 1 to 3 carbon atoms;
R¹ is hydrogen, methyl or ethyl;
R² is alkyl of 1 to 3 carbon atoms;
R³ is phenyl substituted by 1 or 2 substituents selected from the group consisting of methyl, fluorine, chlorine and trifluoromethyl; or naphthyl; and
R⁴ is R⁵CO wherein R⁵ is phenyl unsubstituted or substituted by 1 or 2 substituents selected from the group consisting of alkyl of 1 or 2 carbon atoms, alkoxy of 1 or 2 carbon atoms, trifluoromethyl, nitro, chlorine and fluorine.

8. A compound according to claim 1 wherein
R is methyl;
R¹ is hydrogen;
R² is methyl;
R³ is phenyl substituted by 1 or 2 members selected from the group consisting of methyl, chlorine, or fluorine; and
R⁴ is R⁵CO wherein R⁵ is phenyl substituted by methyl, methoxy, chlorine or trifluoromethyl.

9. A compound according to claim 1 wherein
R is methyl;
R¹ is hydrogen;
R² is methyl;
R³ is phenyl substituted by fluorine, chlorine and methyl or dichlorine; and
R⁴ is chlorobenzoyl, methylbenzoyl, trifluoromethylbenzoyl or methoxybenzoyl.

10. The compound according to claim 1 which is

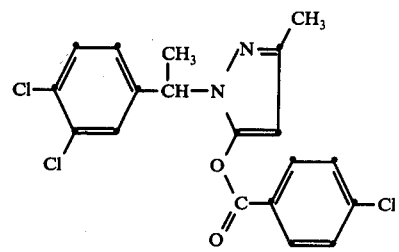

11. The compound according to claim 1 which is

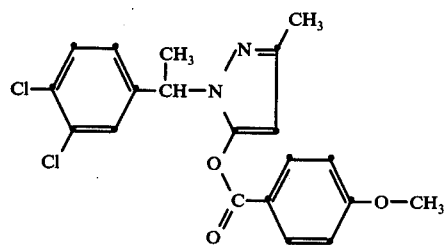

12. The compound according to claim 1 which is

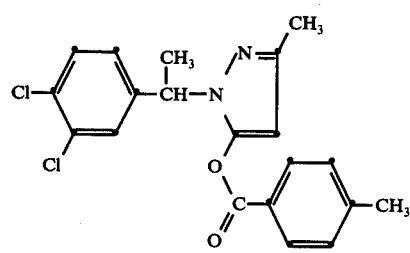

13. The compound according to claim 1 which is

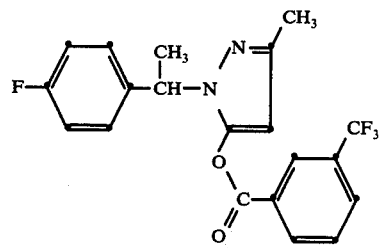

* * * * *